(12) United States Patent
Matter

(10) Patent No.: US 6,443,147 B1
(45) Date of Patent: Sep. 3, 2002

(54) RESPIRATORY CIRCUIT WITH IN VIVO STERILIZATION

(76) Inventor: Jean-Paul Matter, 8385 Indian Hill Rd., Cincinnati, OH (US) 45243

( * ) Notice: Subject to any disclaimer, the term of this patent is extended or adjusted under 35 U.S.C. 154(b) by 0 days.

(21) Appl. No.: 09/206,495

(22) Filed: Dec. 7, 1998

Related U.S. Application Data

(62) Division of application No. 08/994,806, filed on Dec. 19, 1997, now Pat. No. 5,855,203.

(51) Int. Cl.7 .............................................. A61M 16/00
(52) U.S. Cl. ........................... 128/200.26; 128/207.14; 128/207.16; 128/912; 128/909
(58) Field of Search ....................... 128/200.24, 201.27, 128/202.16, 202.25, 202.27, 200.26, 207.14, 207.15, 207.16, 912, 909; 250/455.1

(56) References Cited

U.S. PATENT DOCUMENTS

| | | | |
|---|---|---|---|
| 2,347,954 A | * 5/1944 | Kiely | |
| 2,485,410 A | * 10/1949 | Pope | |
| 3,674,648 A | * 7/1972 | Soli | 128/201.27 |
| 4,433,244 A | * 2/1984 | Hogan | 250/455.1 |
| 4,469,835 A | * 9/1984 | Laurin | 250/455.1 |
| 4,774,415 A | * 9/1988 | Biegel et al. | 250/455.1 |
| 4,834,087 A | 5/1989 | Coleman et al. | 128/207.14 |
| 4,882,496 A | * 11/1989 | Bellotti et al. | 250/455.1 |
| 4,967,743 A | * 11/1990 | Lambert | 128/207.16 |
| 5,053,033 A | 10/1991 | Clarke | 606/3 |
| 5,065,757 A | 11/1991 | Dragisic et al. | 128/207.14 |
| 5,165,395 A | 11/1992 | Ricci | 128/202.22 |
| 5,193,544 A | 3/1993 | Jaffe | 128/634 |
| 5,240,675 A | 8/1993 | Wilk et al. | 422/22 |
| 5,260,020 A | 11/1993 | Wilk et al. | 422/22 |
| 5,503,143 A | 4/1996 | Marion et al. | 128/202.12 |
| 5,507,284 A | 4/1996 | Daneshvar | 128/207.14 |
| 5,565,685 A | 10/1996 | Czako et al. | 250/504 R |
| 5,637,877 A | 6/1997 | Sinofsky | 250/492.1 |
| 5,687,714 A | 11/1997 | Kolobow et al. | 128/207.14 |
| 5,735,271 A | * 4/1998 | Lorenzen et al. | 128/207.16 |
| 5,855,203 A | * 1/1999 | Matter | 128/207.14 |

FOREIGN PATENT DOCUMENTS

| | | |
|---|---|---|
| EP | 0466334 | 1/1992 |
| FR | 2244548 | 4/1975 |
| GB | 1488018 | 10/1977 |

OTHER PUBLICATIONS

PCT International Search Report for PCT/US98/25880 dated Mar. 29, 1999.
Polymer Degradation, Principles and Practical Applications, W. Schnabel, Hanser International, pp. 112–131.
Polymer Chemistry, An Introduction, Second Edition, Malcolm P. Stevens, Oxford University Press 1990, pp. 130–131; pp. 306–311.

(List continued on next page.)

Primary Examiner—Aaron J. Lewis
(74) Attorney, Agent, or Firm—Dinsmore & Shohl LLP

(57) ABSTRACT

A respirator comprise a breathing tube, such as an endotracheal tube, having a proximal end, a distal end, and a lumen extending between the proximal and distal end. The lumen defines at least a portion of the respirator circuit. A ventilator tube is in fluid communication with the proximal end of the breathing tube end and defines a portion of the respirator circuit. One or more light sources capable of emitting ultraviolet radiation irradiates at least a portion of the respiratory circuit, thereby sterilizing the respiratory circuit.

20 Claims, 7 Drawing Sheets

OTHER PUBLICATIONS

New Linear Polymers, Henry Lee, Donald Stoffey, Kris Nevelle, McGraw–Hill Book Company, p. 93.

Respiratory Care, A Guide to Clinical Practice, George F. Burton, M.D., John E. Hodgkin, M.C. and Jeffrey J. Ward, M.Ed., R.R.T., Third Edition J.B. Lippincott Company, 1991, pp. 501, 503.

Results of on–line search of Medline Express®, Records 1–71.

Plastic Component Design, Paul D. Campbell, 1996, Industrial Press Inc., pp. 117–119.

Evidence for Dynamic Phenomena in Residual Tracheal Tube Biofilm, British Journal of Anaesthesia, Jan. 1993, vol. 70, No. 1.

Concise Clinical Study, Contaminated Condensate in Mechanical Ventilator Circuits, Donald E. Craven, Theresa A. Goularte, Barry J. Make, Boston, Massachusetts, 1984, pp. 625–628.

Effect of Aerosolization on Culturability and Viability of Gram–Negative Bacteria, J. F. Heidelberg, M. Shahamat, M. Levin, I. Rahman, G. Stelma, C. Grim and R. R. Colwell, Applied and Environmental Microbiology, Sep. 1997, vol. 63, No. 3, pp. 3585–3588.

Nosocomial pulmonary infection: Possible etiologic significance of bacterial adhesion to endotracheal tubes, Frank D. Sottile, Thomas J. Marrie, Donald S. Prough, Cherri D. Hobgood, David J. Gower, Lawrence X. Webb, J. William Costerton, Anthony G. Gristina, Critical Care Medicine, 1986, vol. 14, No. 4, pp. 265–270.

Ballard Medical Products: TrachCare, Ballard Medical Website visited on Dec. 2, 1998, http://www.bmed.com/products/trachcare.shtml, pp. 1–6.

* cited by examiner

RESPIRATORY CIRCUIT WITH IN VIVO STERILIZATION

This is a divisional application of Ser. No. 08/994,806 filed Dec. 19, 1997, now U.S. Pat. No. 5,855,203.

TECHNICAL FIELD

The present invention relates generally to breathing devices, and will be specifically disclosed as a respiratory circuit capable of in vivo sterilization.

BACKGROUND OF THE INVENTION

In many medical situations, the pulmonary functions (i.e., relating to the lungs) of a patient need to be monitored, controlled or accessed, and in many circumstances for days at a time. To achieve this, the medical field often uses a respiratory circuit which is connected to a ventilator, which is sometimes referred to as a respirator. Typically, respiratory circuits include a breathing tube (e.g. endotracheal tubes, tracheostomy tubes, laryngeal mask airways, and the like) that acts as the interface between the patient and the respiratory circuit. For instance, an endotracheal tube is inserted through the mouth or nasal passages of the patient and into the trachea. Usually, a balloon or cuff surrounding the inserted end of the tube is inflated to provide a seal between the endotracheal tube and the trachea. Once sealed, the patient breathes through the endotracheal tube.

Once a breathing tube is connected to a patient, other components of the respiratory circuit are coupled to the breathing tube. Usually, a ventilator tube links the breathing tube with a ventilator which monitors, and if necessary can control, the pulmonary functions of the patient. Other components, such as junctions, moisture traps, filters, humidifiers and the like, optionally can be added to the respiratory circuit. For instance, drug delivery systems can be added to the respiratory circuit to delivery aerosolized medicine to the lungs of the patient. In some circumstances, medical care givers require access to the lungs and/or trachea of the patient. For example, suction catheters are used to remove secretions in a patient's lungs. In such circumstances, special junctions can be added to the respiratory circuit which allow such access without interrupting the monitoring or control of the pulmonary functions.

An ongoing challenge with respiratory circuits is maintaining a sterile environment. Indeed, one clinical study has concluded that "trying to maintain a sterile ventilator circuit for 24 hours is a difficult and perhaps impossible task." Contaminated Condensate in Mechanical Ventilator Circuits, Donald E. Craven, et al., Concise Clinical Study, p. 627. Due to the inherent moisture and warmth, respiratory circuits provide superb conditions for microbiological growth or colonization. Once colonization has started, the microbiological growth can easily spread to the patient, either airborne or through moisture condensation running down into the patient's lungs, thus risking infections and complications, often resulting in pneumonia.

The problem of respiratory circuit colonization is especially prevalent within breathing tubes. For instance, studies has documented the health risks from colonization in endotracheal tubes, sometimes called a biofilm, which can be so extensive that the walls of the endotracheal tube become slimy and sticky. See Nosocomial pulmonary infection: Possible etiologic significance of bacterial adhesion to endotracheal tubes, Frank D. Sottile et al., Critical Care Medicine, Vol. 14, No. 4, p. 265. Due to the close proximity to the patient's lungs, any microbiological growth in a breathing tube can easily spread to the patient's lungs. Condensed moisture can run down the breathing tube, over the biofilm and into the patient's lungs. Additionally, chunks of the biofilm can actually fall off the breathing tube and into the patient's lungs.

SUMMARY OF THE INVENTION

Accordingly, an object of the invention is to provide an improved respirator circuit.

Another object of the invention is to provide a respirator circuit capable of sterilization while connected to a patient.

Still another object of the present invention is to provide an endotracheal tube capable of in vivo sterilization.

Yet another object of the present invention is to provide a respirator circuit junction capable of vivo sterilization.

Additional objectives, advantages and novel features of the invention will be set forth in the description that follows and, in part, will become apparent to those skilled in the art upon examining or practicing the invention. The objects and advantages of the invention may be realized and obtained by means of the instrumentalities and combinations particularly pointed out in the appended claims.

One aspect of the present invention is an apparatus for in vivo sterilization of a respiratory circuit. A breathing tube has a proximal end, a distal end and a lumen extending between the proximal and distal ends. The lumen defines at least a portion of a respiratory circuit. A ventilator tube is in fluid communication with the proximal end of the breathing tube. The ventilator tube defines at least a portion of the respiratory circuit and has an inhalation portion and exhalation portion. One or more light sources irradiate at least a portion of the respiratory circuit. The light sources emit ultraviolet radiation for sterilizing the respiratory circuit.

Another aspect of the present invention is an endotracheal tube. A tube is adapted for insertion into the trachea of a patient. The tube has a proximal end, a distal end, and a tube wall having an inner surface and an outer surface. A light source emits ultraviolet radiation. The light source is positioned relative to the tube to bathe at least a portion of the inner surface of the tube wall with ultraviolet radiation.

Still another aspect of the present invention is a respiratory circuit junction. A tube port is adapted to interface with a breathing tube. A line port is adapted to interface with a ventilator line. A flow path extends between the tube and line ports. A catheter having a proximal end and a distal end is received by a catheter port connected to the flow path. The catheter port is dimensioned such that the catheter can be axially moved relative to the catheter port. The catheter port is aligned relative to the tube port such that the distal end of the catheter can be inserted into a breathing tube connected to the tube port. A light source capable of emitting ultraviolet radiation is positioned to irradiate at least a portion of the catheter.

Still other aspects of the present invention will become apparent to those skilled in the art from the following description of a preferred embodiment, which is by way of illustration, one of the best modes contemplated for carrying out the invention. As will be realized, the invention is capable of other different and obvious aspects, all without departing from the invention. Accordingly, the drawings and descriptions are illustrative in nature and not restrictive.

BRIEF DESCRIPTION OF THE DRAWINGS

The accompanying drawings, incorporated in and forming part of the specification, illustrate several aspects of the present invention and, together with their descriptions, serve to explain the principles of the invention. In the drawings.

Reference will now be made to the present preferred embodiment of the invention, an example of which is illustrated in the accompanying drawings, wherein like numerals indicate the same element throughout the views.

DETAILED DESCRIPTION

Figure 1:
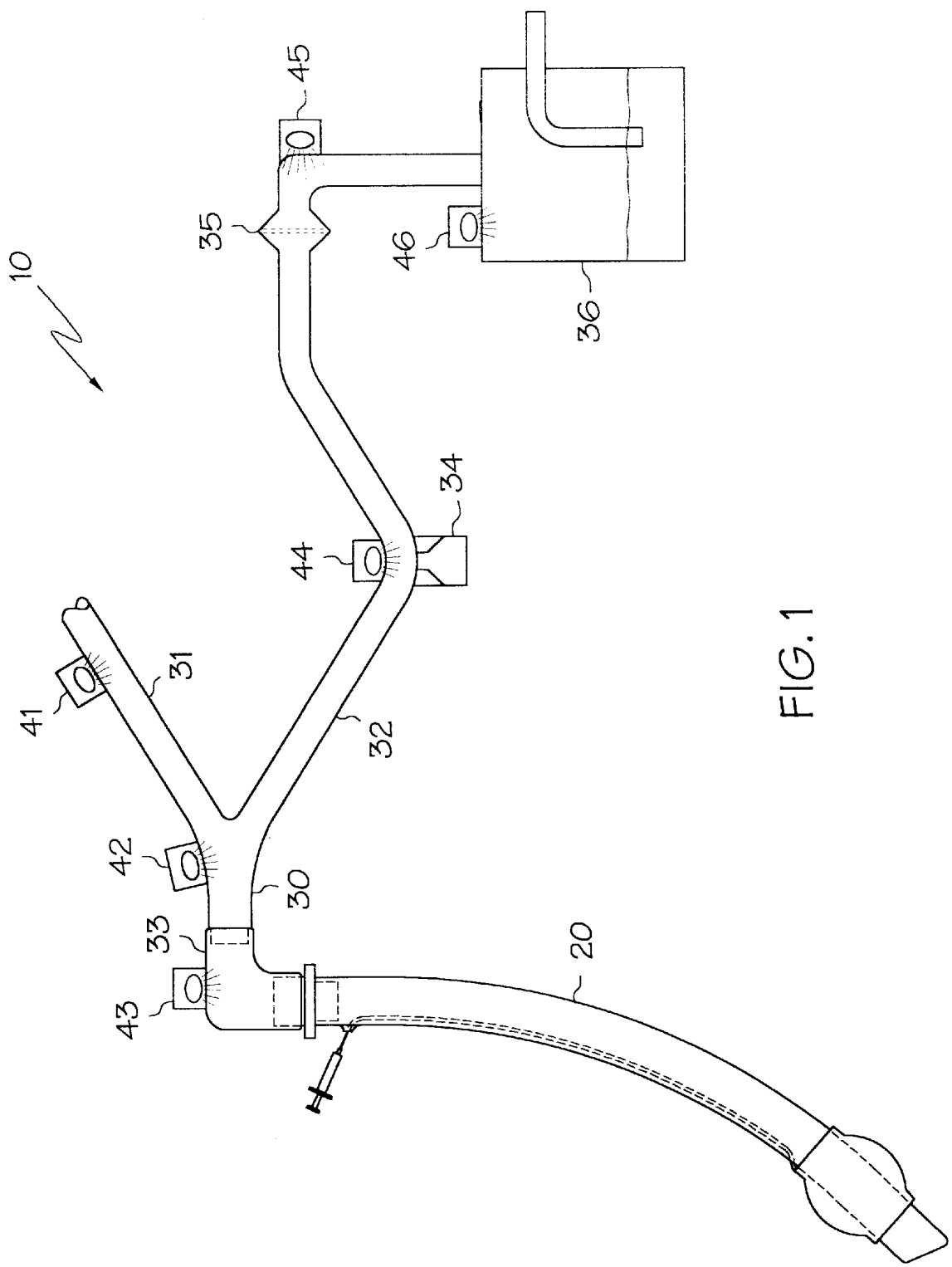
FIG. 1 depicts a schematic view of a respiratory circuit capable of in vivo sterilization.

One embodiment of the present invention is depicted in FIG. 1, which illustrates an example of a respiratory circuit 10. A breathing tube 20, shown here as an endotracheal tube, forms a portion of the respiratory circuit 10. A ventilator tube 30 also forms a portion of the respiratory circuit 10. The ventilator tube 30 includes an exhalation portion 31 and an inhalation portion 32. The ventilator tube 30 is connected to a ventilator (not shown), which can be used to monitor and/or control the pulmonary functions of a patient. Valves and control mechanisms in the ventilator direct whether the exhalation portion 31 or the inhalation portion 32 will be used during a breath cycle. The ventilator tube 30 is in fluid communication with the breathing tube through the junction 33. A variety of components are connected to the ventilator tube 30. The moisture trap 34 is used to collect any condensation buildup in the ventilator tube 30. A filter 35 is located within the flow passage of the ventilator tube 30 and is used to filter air passing through the inhalation portion 32. The humidifier 36 is used to add moisture to air in the inhalation portion 32.

One or more light sources 41–45 are positioned so as to irradiate at least a portion of the respiratory circuit 10. The light sources can remain on at all times while the respiratory circuit is in use, or alternatively could be intermittently activated. The light sources emit ultraviolet radiation which sterilizes those portions of the respiratory circuit which are being irradiated as well as the air flowing in the respiratory circuit. Preferably, the light sources will emit light ranging from 200 to 400 nanometers in wave length. Ultraviolet radiation is capable of sterilizing both airborne and surface microbiological growth. For instance, studies have indicated that the sterilization efficacy of ultraviolet radiation in standard air flow conditions (0.5 second irradiation) were found to be over 99.5% in staphylococcus aureus, staphylococcus epidermidis, serratia marcescens, bacillus subtilis (vegetative cell) and bacillus subtilis (spore), and 67% in aspergillus niger (conidium). In aspergillus niger, which was the most resilient microbe to ultraviolet radiation, the efficacy rose up to 79% when irradiated for one second.

Preferably, the light sources are strategically positioned in the respiratory circuit 10 so as to sterilize the most critical areas. For instance, the light source 41 is located in the exhalation portion 31 of the ventilator tube. The light source 42 is positioned so as to irradiate the Y junction between the exhalation portion 31 and the inhalation portion 32 within the ventilator tube 30. The light source 43 is located so as to irradiate the junction 33 and so as to irradiate the lumen of the breathing tube 20. The light source 44 positioned so as to irradiate the moisture trap 34. The light source 45 irradiates the filter 35 and the light source 46 irradiates the humidifier 36. Beyond these respirator components, ultraviolet light sources can be positioned to irradiate other components, such as artificial noses, nebulizers, etc. As one with ordinary skill in the art will readily appreciate, more or fewer light sources could be used to achieve the objectives of the present invention.

Figure 2:
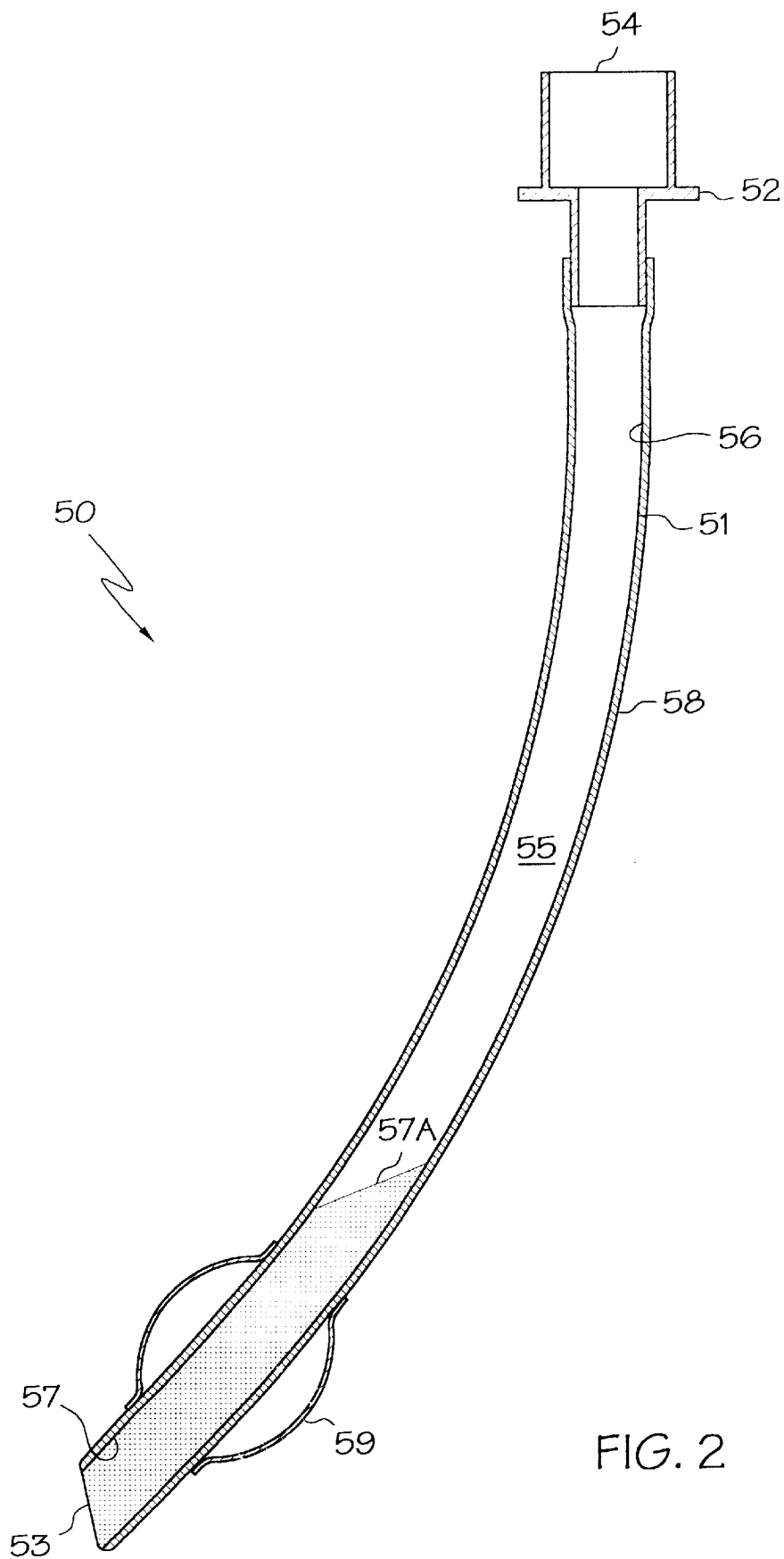
FIG. 2 depicts an endotracheal tube capable of in vivo sterilization.

FIG. 2 illustrates an endotracheal tube 50 which may be used in place of the breathing tube 20. The endotracheal tube 50 comprises a tube wall 51, which is connected to the interface 52 dimensioned to connect to other components of a ventilator circuit. The endotracheal tube has a distal end 53 and a proximal end 54 with a lumen 55 extending between the proximal 54 and distal 53 ends. The cuff 59 is a balloon which surrounds the tube wall 51 near the distal end 53 to provide a seal once the endotracheal tube is inserted in the trachea of a patient. The cuff can be inflated and deflated through a tube (not shown,) preferably located within the tube wall 51, with a device such as a syringe (not shown).

Preferably, when connected to the other parts of the respiratory circuit 10, light source 43 is positioned so as to irradiate the proximal end 54 such that ultraviolet radiation enters the lumen 55. A reflective portion 56 on the inner surface of the tube wall 51 reflects the ultraviolet radiation that enters the lumen 55. The reflective properties of the inner surface portion 56 can come from a coating or alternatively through a reflective composite within the tube wall 51. For instance, particulates of aluminum or silver can be suspended in the tube wall 51 to provide adequate reflective properties. When ultraviolet radiation enters the lumen 55 and strikes the reflective portion 56, the ultraviolet radiation will reflect and disperse within the lumen 55 and propagate towards the distal end 53, thus bathing the inner surface of the tube wall 51 with ultraviolet radiation.

The ultraviolet absorbent portion 57 of the inner surface of the tube wall 51 will absorb substantial portions of the reflected ultraviolet radiation, thus preventing ultraviolet radiation from exiting through the distal end 53. Like the reflective portion 56, the absorbent portion 57 can be a coating or suspended within the tube wall 51. One suitable composition is graphite suspended within the tube wall 51. Preferably, the absorbent portion 57 will have a beveled interface 57A with the reflective portion 56 so as to control the amount of ultraviolet radiation exiting the absorbent port 57 while minimizing the amount of ultraviolet radiation exiting the distal end 53. The amount of ultraviolet radiation leaving the distal and 53 can be further controlled by intermittently activating the light source or controlling the intensity of the light source so as to provide only the desired results.

As the ultraviolet radiation strikes the reflective portion 56 and the absorbent portion 57, the inner surface of the tube wall 51 will be sterilized, thus preventing colonization in the endotracheal tube 50. While the reflective portion 56 and the absorbent portion 57 are preferably ultraviolet opaque (i.e., substantially impervious to the passage of ultraviolet radiation), the outer surface 58 of the tube wall 51 can optionally include an ultraviolet absorbing coating to further prevent any ultraviolet radiation within the lumen 55 from irradiating through the tube wall 51 and striking the patient. The interface 52 also preferably has ultraviolet opaque qualities.

Figure 3:
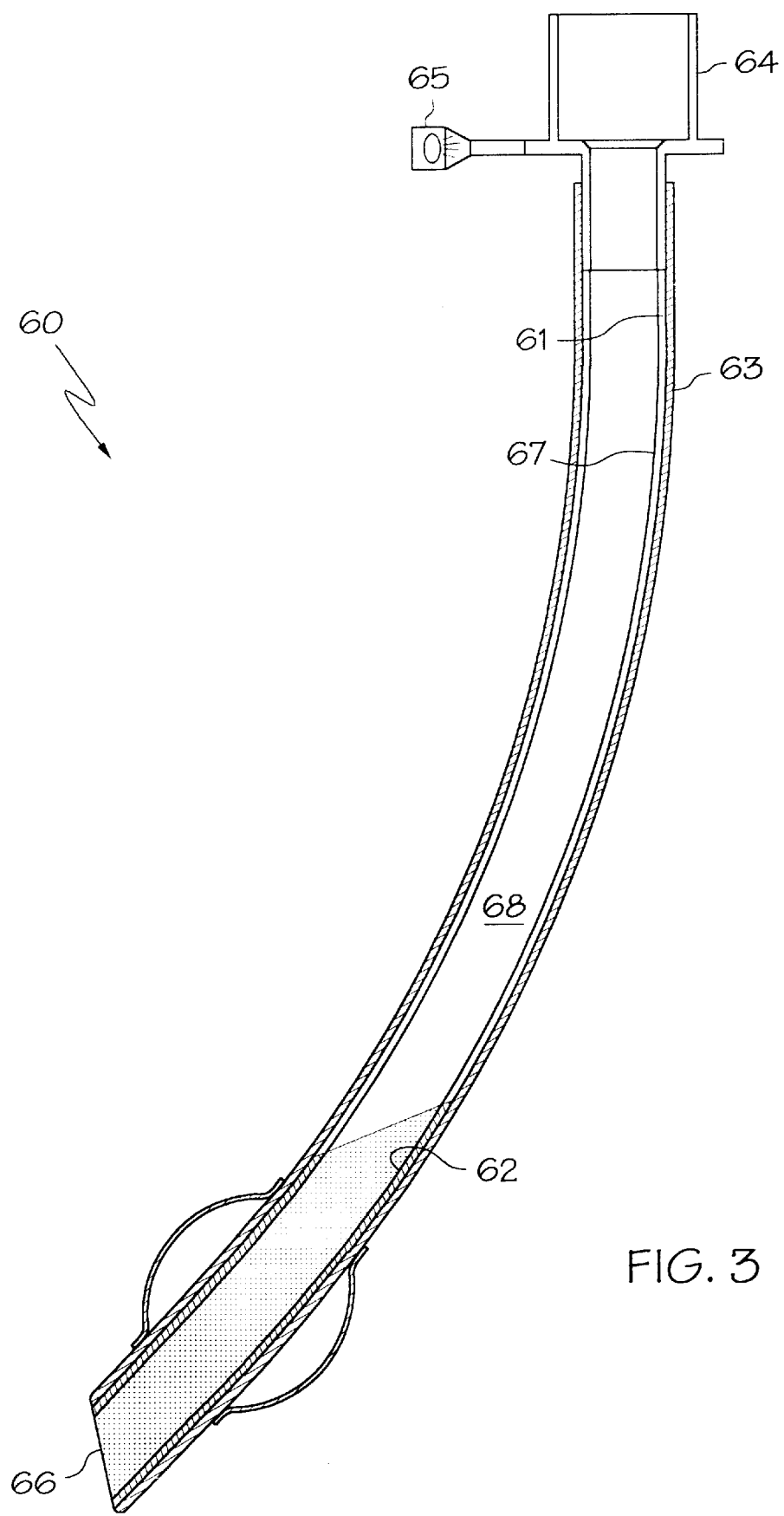
FIG. 3 depicts an alternative embodiment of an endotracheal tube capable of in vivo sterilization.

FIG. 3 depicts an alternative embodiment of an endotracheal tube 60. The endotracheal tube includes an inner tube wall 61 and an outer tube wall 63. The two tube walls 61, 63 are connected to the interface 64. An ultraviolet light source 65 is optically coupled with the interface 64, and the interface 64 is optically coupled with the inner tube wall 61. Both the interface 64 and the inner tube wall 61 are made from a light transmissive material such that radiation emanating from the light source 65 passes through the interface 64 and into the inner tube wall 61. The inner tube wall 61 acts as an optical path for the ultraviolet radiation. The outer tube wall 63, which can take the form of a coating around the inner tube wall 61, has ultraviolet opaque qualities such that light within the inner tube wall 61 will not irradiate through the outer tube wall 63 and strike the patient. Ultraviolet radiation within the inner tube wall 61 will illuminate the inner surface 67 thereby sterilizing the endotracheal tube 60.

The portion 62 oft he inner tube wall 61 near the distal end 66 of the endotracheal tube 60 also has ultraviolet opaque qualities. As such, ultraviolet radiation traveling longitudinally along the inner tube wall 61 will be prevented from traveling the entire length of the inner tube wall 61 and exiting the distal end 66. Any ultraviolet radiation irradiating from the inner tube wall 61 into the lumen 68 will strike the absorptive portion 62 thus preventing ultraviolet radiation in the lumen 68 from exiting the distal end 66.

The amount of ultraviolet radiation entering the lumen 68 from the inner tube wall 61 can be increased by adding particulates within the inner tube wall 61. When the ultraviolet radiation traveling through the optical path strikes these particulates, the light will be diffused and exit the inner tube wall 61 to strike the inner surface 67. Beyond the embodiment shown in FIG. 3, the light source 65 could be directly coupled to the inner tube wall 61 thus bypassing the interface 64. Alternatively, discrete optical paths in the form of light fibers located in the inner tube wall 61 or adjacent the inner surface 67 could be used to sterilize the endotracheal tube.

Figure 4:
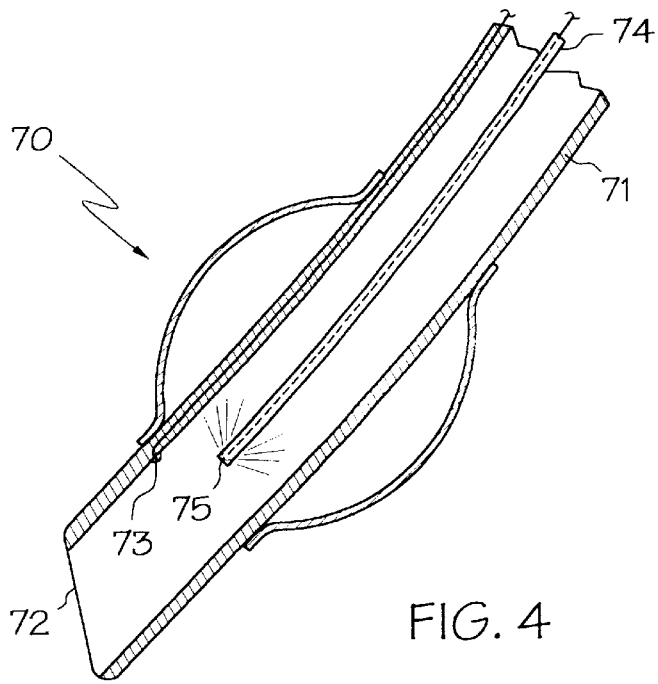
FIG. 4 depicts another embodiment of an endotracheal tube capable of in vivo sterilization.

FIG. 4 depicts another embodiment of an endotracheal tube capable of in vivo sterilization. In one embodiment, the endotracheal tube 70 has a tube wall 71 with ultraviolet opaque qualities. Preferably, the tube wall 71 is substantially absorbative to ultraviolet radiation, thereby preventing the propagation of ultraviolet radiation within the endotracheal tube 70. The light catheter 74 is coupled to a ultraviolet radiation light source (not shown) and the catheter 74 is inserted in the endotracheal tube. Preferably, ultraviolet radiation will only emanate from the distal tip 75 of the catheter 74, and ideally, only in the proximal direction to prevent ultraviolet radiation from exiting the distal end 72. Preferably, the length of the catheter 74 is limited so as to prevent the distal end 75 of the catheter from extending beyond the distal end 72 of the endotracheal tube. Located near the distal end 72 of the endotracheal tube is an optional ultraviolet radiation sensor 73. The ultraviolet sensor 73 is an additional precaution to prevent ultraviolet radiation from exiting the distal end 72 of the endotracheal tube. When a predetermined amount of ultraviolet radiation strikes the sensor 73, a signal is sent to the proximal end (not shown) of the endotracheal tube and the light source is automatically turned off.

Figure 4A:
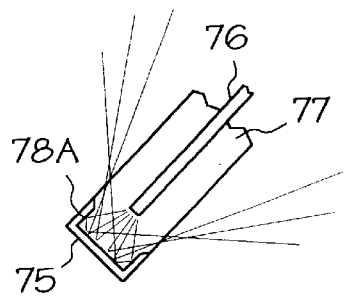
Figure 4B:
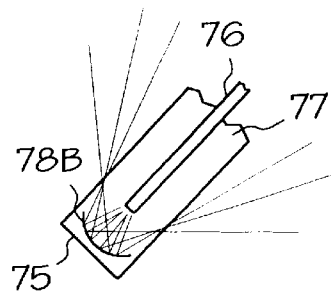
Figure 4C:
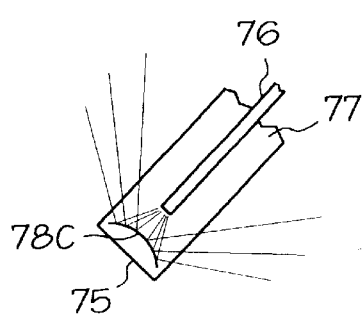
Figure 4D:
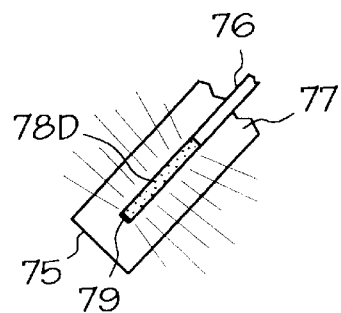

FIGS. 4A–4D illustrate several embodiments of the light catheter 74 which can provide directional diffusion of ultraviolet radiation. All of the illustrated catheter embodiments share a light delivery fiber 76 which is directly coupled to an ultraviolet light source (not shown). All the illustrated embodiments also share a catheter wall 77 surrounding the fiber 76, which wall 77 is at least partially transparent adjacent the diffuser 78A–D. As shown in FIG. 4A, ultraviolet light traveling along the light delivery fiber 76 will strike the cap diffuser 78A which will in turn reflect and diffuse the light in the proximal direction. FIGS. 4B and 4C illustrate a concave and convex embodiments of the reflective diffusers 78B and 78C, respectively, which are encased within the catheter wall 77. FIG. 4D illustrates a diffuser 78D which is directly coupled with the light delivery fiber 76. Particles are embedded with in the diffuser 78D such that light will strike the particles and reflect away from the diffuser. A cap piece 79 prevents ultraviolet radiation from exiting the distal end 75 of the catheter 74.

The light catheter 74 is used by first inserting the distal end 75 into a standard catheter port in a ventilator circuit. The light source is then activated. The distal end 75 is then pushed down into the endotracheal tube 70 until it reaches close to the distal end 72. Then, the catheter is pulled out from the endotracheal tube in the reverse order. As the distal end 75 is inserted and pulled from the tube 70, the ultraviolet radiation will strike the inner surface of the tube wall 71 thus sterilizing it and preventing colonization and the buildup of biofilm. This catheter sterilization process is performed periodically while a patient is intubated. Preferably, the sterilization process will be preformed once every hour. In another embodiment, the tube wall 71 is at least partially transparent such that the outer surface of the tube wall will be sterilized.

Figure 5:
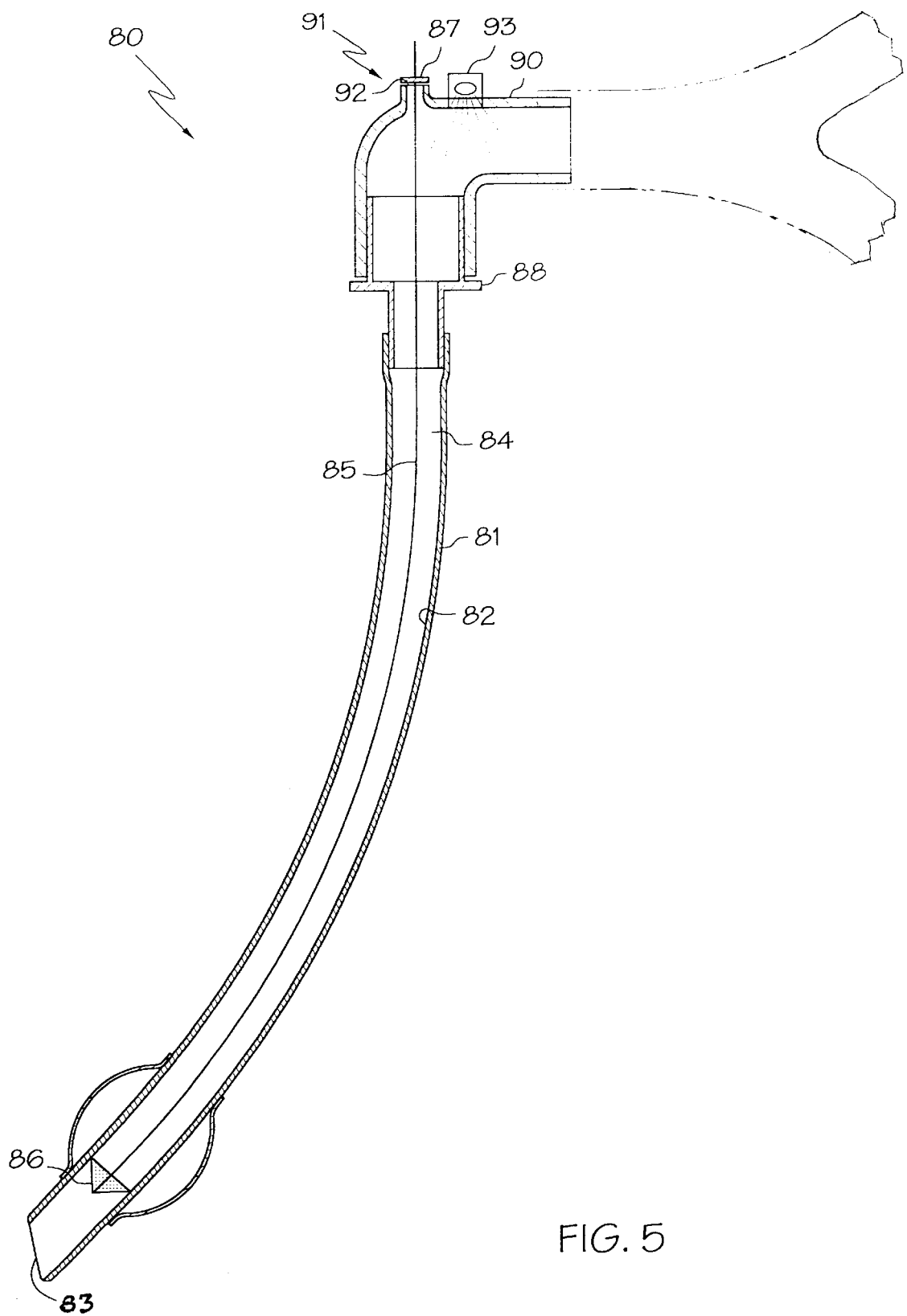
FIG. 5 depicts yet another embodiment of an endotracheal tube capable of in vivo sterilization.

FIG. 5 depicts another embodiment of an endotracheal tube 80. The endotracheal tube 80 comprises a tube wall 81 which is connected to the interface 88. The interface 88 is connected to a junction 90 having a catheter port 91. When the endotracheal tube requires sterilization, the filter probe 85 is inserted into the lumen 84, as shown. The filter probe 85 has a filter 86 which allows air to pass through but blocks ultraviolet radiation. The junction 90 further comprises a light source 93 capable of emitting ultraviolet radiation, which is activated when the filter probe 85 is located in the endotracheal tube 80. The light source 93 is positioned such that the ultraviolet radiation will irradiate the lumen 84 of the endotracheal tube 80. The inner surface 82 of the tube wall 81 is preferably reflective and opaque such that the ultraviolet radiation will propagate towards the distal end 83 of the endotracheal tube, thus bathing the inner surface 82 with sterilizing ultraviolet radiation. The filter 86 prevents ultraviolet radiation from exiting through the distal end 83.

Preferably, the filter 86 is substantially air permeable and made from a resilient foam or fibrous material capable of being biased to the inner surface 82 of the endotracheal tube wall 81. Ideally, the filter 86 is compressible enough to fit through the catheter port 91. Optionally, the filter probe 85 includes a bar 87 or other blocking mechanism prevent the filter 86 from extending beyond the distal end 83. Preferably, the light source 93 will only illuminate when the bar 87 engages the contact 92 to complete an electrical circuit. As such, the light source 93 automatically activates only when the probe 85 is fully inserted in the endotracheal tube 80. After the inner surface is sterilized, the probe 85 is removed, thus deactivating the light source 93, and disposed. The catheter port 91 can then be capped.

Figure 6:
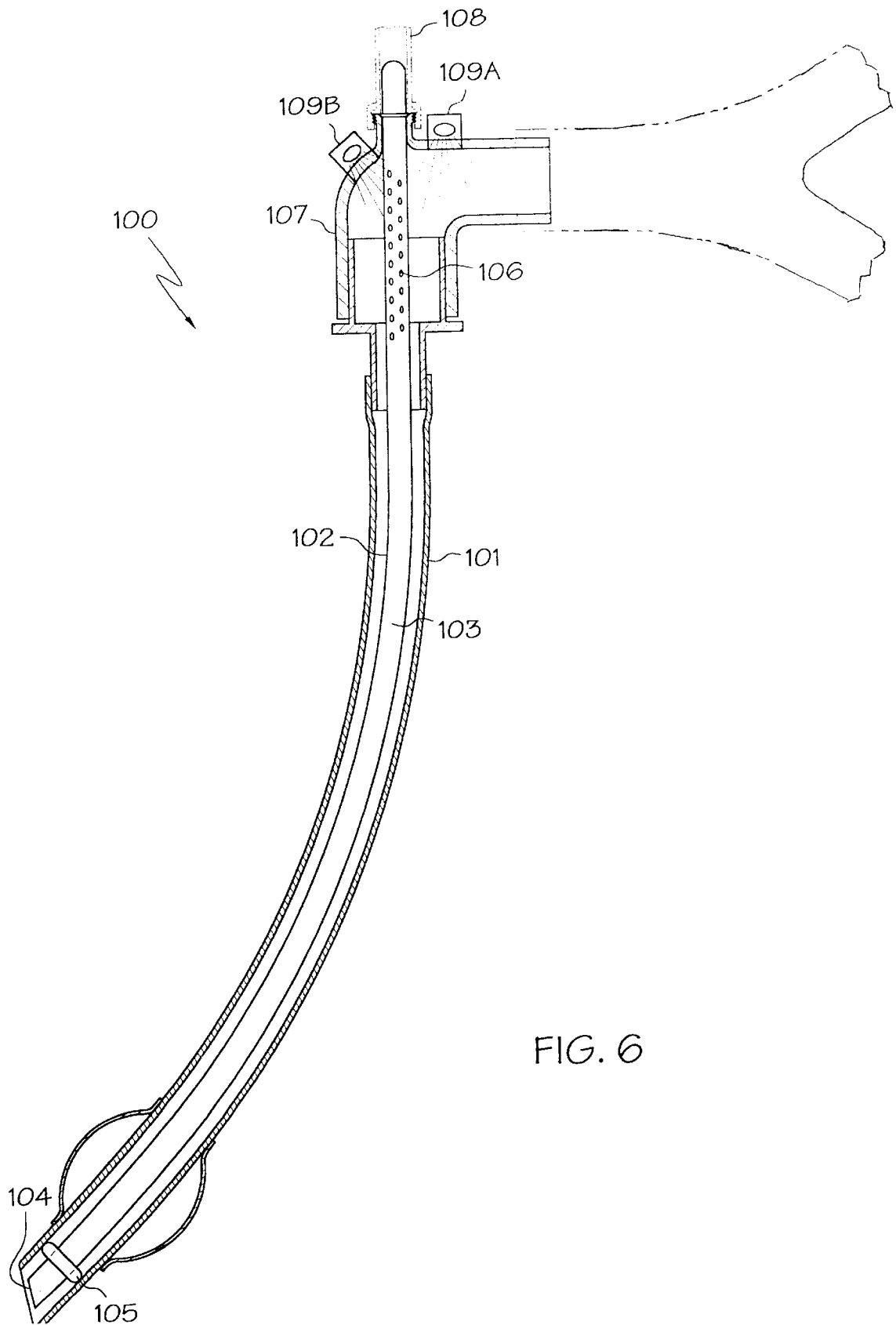
FIG. 6 depicts still another embodiment of an endotracheal tube capable of in vivo sterilization.

FIG. 6 depicts another embodiment of an endotracheal tube 100. The endotracheal tube 100 includes a tube wall 101. When the endotracheal tube requires sterilization, the inner tube 102 is inserted within the tube wall 101. The inner tube 102 includes a cuff 105 which when inflated provides a seal between the inner tube 102 and the tube wall 101. When the cuff 105 is inflated, the patient breathes through the lumen 103 of the inner tube 102, which extends between the vent holes 106 and the open distal end 104 of the inner tube 102. In this position, the light source 109A, which emits ultraviolet radiation, irradiates the inner surface of the tube wall 101 thereby sterilizing the endotracheal tube. The outer surface of the inner tube 102 and/or the inner surface of the outer tube 101 are reflective and opaque to help propagate ultraviolet radiation within the endotracheal tube. The cuff 105 is opaque and prevents ultraviolet radiation from exiting the distal end of the endotracheal tube. Optionally, the junction 107 is adapted for receiving the inner tube 102 and includes a sleeve 108 to maintain the inner tube 102 in the sterile environment when not inserted within the tube wall 101. The junction 107 also includes the light source 109B which is positioned so as to irradiate the inner tube 102 as it is inserted and removed from the tube wall 101.

Figure 7:
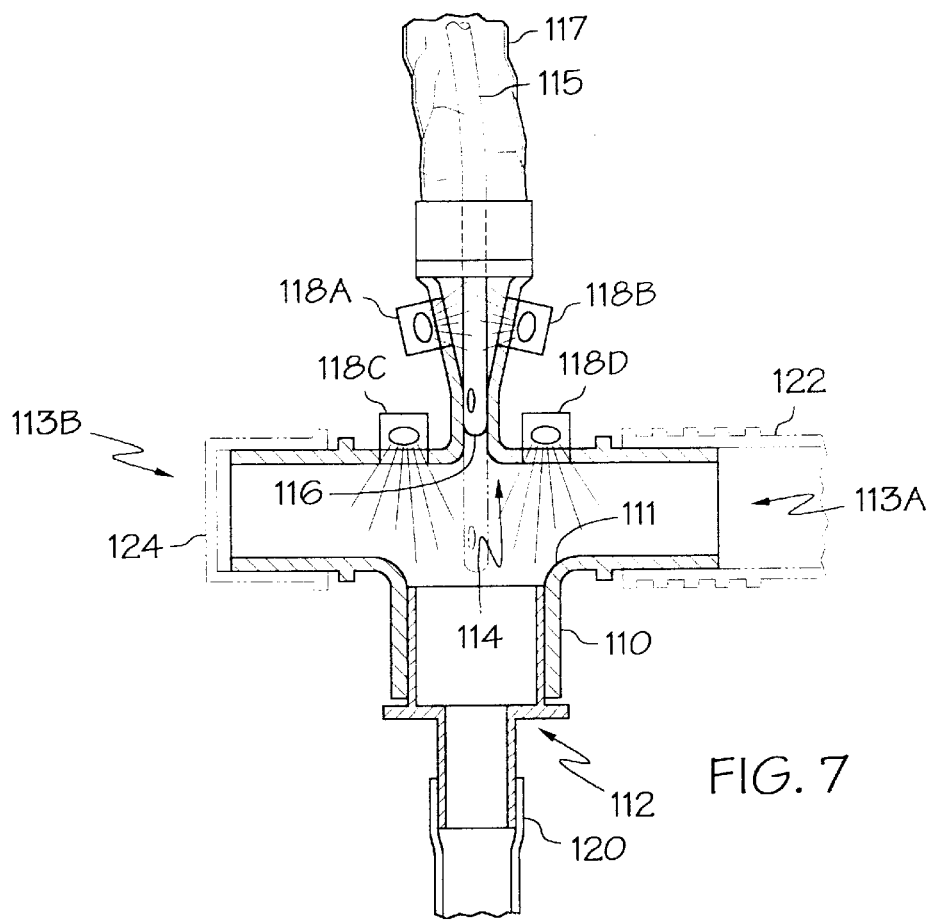
FIG. 7 depicts a respiratory circuit junction with a suction catheter capable of in vivo sterilization.

FIG. 7 depicts a junction 110 in a respiratory circuit. The junction 110 includes a tube port 112, which is adapted to receive a breathing tube 120, such as an endotracheal tube. The junction 110 includes two line ports 113A and 113B which are adapted to receive various components for a respiratory circuit. For instance the line port 113A is connected to a ventilator line 122 and the line port 113B is connected to a cap 124. Other such attachments include metered dose inhalers, swivel couplings, and the like. The catheter port 114 receives the catheter 115 and is dimensioned such that the catheter can move axially relative to the catheter port 114, as demonstrated in phantom. The catheter port 114 is aligned relative to the breathing tube 120 such that the catheter 115 can be inserted into the breathing tube 120. In this embodiment, catheter 115 is a suction catheter which is adapted to be inserted into the breathing tube 120 and into the patient's lungs to remove secretions or fluid. The tip 116 of the catheter 115 includes several openings to allow such suction.

In its fully retracted position, as shown in FIG. 7, the catheter 115 is stored in a flexible sleeve 117, which maintains the catheter 115 in the sterile environment while not being use. The light sources 118A–D are capable of emitting ultraviolet radiation. The light sources 118A and 118B are positioned adjacent the catheter port 114 to irradiate the catheter 115. As such, when the catheter 115 is inserted into or retracted from the breathing tube 120, a substantial length of the inserted catheter 115 will be irradiated with ultraviolet radiation thus sterilizing it. Preferably, the catheter 115 is at least partially transparent so the ultraviolet radiation will sterilize both the outer surface and the inner surface of the catheter 115. The light sources 118C and 118D are positioned so as to irradiate the inner surface 111 of the junction 110 and also to irradiate the lumen of the breathing tube 120. Preferably the wall 110 of the junction is opaque, except where the light sources 118A–D are located. In this embodiment, the inner surface 111 is reflective so as to encourage the propagation and bathing of the inner surface 111 with ultraviolet radiation.

Figure 8A:
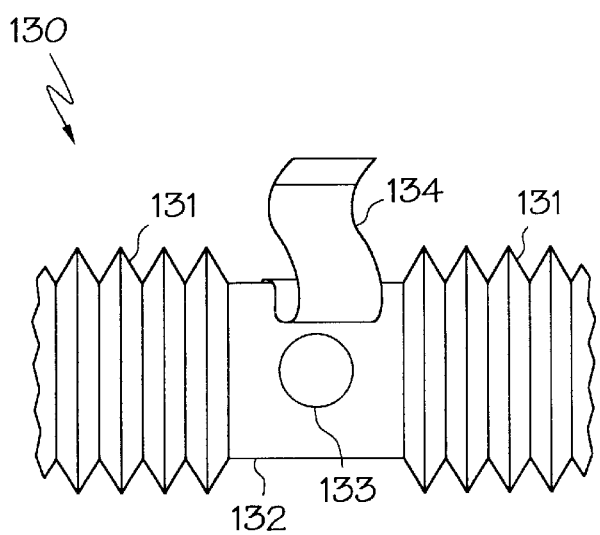
FIG. 8 depicts a ventilator tube capable of in vivo sterilization.
Figure 8B:
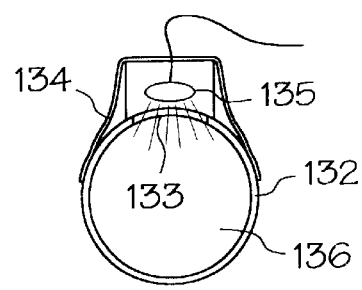

FIG. 8A depicts a portion of a ventilator line 130. The flexible portions 131 are integrally connected to the cylindrical portion 132. The ventilator tube wall, including both the flexible portion 131 and the cylindrical portion 132, is ultraviolet opaque which prevents ultraviolet radiation from escaping through the walls. Preferably, the tube wall is reflective to encourage the propagation of ultraviolet radiation along the ventilator tube. The window 133, however, does permit ultraviolet radiation from passing through. As depicted in FIG. 8B, the window 133 is adapted to receive a light source 135 capable of emitting ultraviolet radiation. When not in use, the tape 134, which is capable of blocking ultraviolet radiation, covers the window 133 thus preventing ultraviolet radiation within the tube from escaping through the window 133. The tape 134 can also be used to secure the light source 135 to the cylindrical portion 132. Other windows can be located throughout the ventilator tube wherever sterilization is desired. Similar variations of the embodiment illustrated in FIG. 8 can be easily adapted to sterilized various components within the respirator circuit, such as moisture traps, filters, humidifiers, and the like.

Throughout the foregoing specification, the materials used in the junctions, ventilator tubes, breathing tubes, etc. are designed to be irradiated with ultraviolet radiation, which can be destructive to many materials. As such, preferred materials will be resistant to ultraviolet radiation, either through their inherence qualities, such as Teflon, or through additives used as ultraviolet absorbers or antioxidants. While one with ordinary skill in the art will be capable of selecting such preferred materials or additives, the following references maybe helpful: *Polymer Degradation Principles* and *Practical Applications* by W. Schnabel, *Polymer Chemistry and Introduction Second Edition* by Malcolm P. Stevens, *New Linear Polymers* by Henry Lee, et al., and *Plastic Component Design* by Paul Campbell, which references are hereby incorporated by reference.

The foregoing description of the preferred embodiment of the invention has been presented for purposes of illustration and description. It is not intended to be exhaustive nor to limit the invention to the precise form disclosed. Many alternatives, modifications, and variations will be apparent to those skilled in the art in light of the above teaching. Accordingly, this invention is intended to embrace all alternatives, modifications, and variations that fall within the spirit and broad scope of the amended claims.

We claim:
1. A respiratory circuit junction, comprising:
    a) a tube port adapted to interface with a breathing tube;
    b) a line port adapted to interface with a ventilator line;
    c) a flow path extending between the tube and line ports;
    d) a catheter having a proximal end and a distal end;
    e) a catheter port connected to the flow path for receiving the catheter such that the catheter can be axially moved relative to the catheter port, said catheter port being aligned relative to the tube port such that the distal end of the catheter can be inserted into a breathing tube connected to the tube port;
    f) a light source positioned to irradiate at least a portion of the catheter, said light source being capable of emitting ultraviolet radiation; and
    g) an ultraviolet opaque portion operative to absorb ultraviolet radiation within the respiratory circuit junction to prevent a substantial portion of ultraviolet radiation from exiting the junction and striking a patient.

2. A respiratory circuit junction as recited in claim 1, wherein the catheter is a suction tube.

3. A respiratory circuit junction as recited in claim 1, wherein the light source is located adjacent the catheter port.

4. A respiratory circuit junction as recited in claim 1, wherein at least a portion of the inner surface of the respiratory circuit junction is reflective to ultraviolet light.

5. A respiratory circuit junction as recited in claim 1, wherein one or more light sources are located adjacent to the line port.

6. A respiratory circuit junction as recited in claim 1, further comprising an additional line port.

7. A respiratory circuit junction as recited in claim 6, wherein one or more light sources are located adjacent to the additional line port.

8. A respiratory circuit junction as recited in claim 6, further comprising a metered dose inhaler unit coupled to the additional line port.

9. A respiratory circuit junction as recited in claim 6, further comprising a swivel coupling coupled to the additional line port.

10. A respiratory circuit junction as recited in claim 6, further comprising an optical path located in the flow path extending between the tube and line ports, wherein said light source is optically connected to said optical path.

11. A respiratory circuit junction as recited in claim 10, wherein the light source irradiates through the respiratory circuit junction towards the breathing tube.

12. A method for in vivo sterilization of a respiratory circuit unction, comprising the steps of:
   a) inserting a breathing tube in the trachea of a patient;
   b) connecting a respiratory circuit junction to the breathing tube, said respiratory circuit junction having an inner surface defining a flow path and a catheter port with a catheter positioned therein;
   c) irradiating at least a portion of the inner surface of the respiratory circuit junction with ultraviolet radiation to sterilize the inner surface while the respiratory circuit junction is connected to the breathing tube; and
   d) absorbing the ultraviolet radiation to prevent a substantial portion of radiation from leaving the respiratory circuit junction and striking the patient.

13. A method of in vivo sterilization of a respiratory circuit junction as recited in claim 12, wherein the step of irradiating is performed intermittently.

14. A method of in vivo sterilization of a respiratory circuit junction as recited in claim 12, wherein the step of irradiating comprises positioning an ultraviolet light source external to the respiratory circuit junction and bathing the inner surface with ultraviolet radiation from the light source.

15. A method of in vivo sterilization of a respiratory circuit junction as recited in claim 12, further comprising the step of connecting the respiratory circuit junction to a metered dose inhaler unit.

16. A method of in vivo sterilization of a respiratory circuit junction as recited in claim 12, further comprising the step of connecting the respiratory circuit junction to a swivel coupling.

17. A respiratory circuit junction, comprising:
   a) a tube port in fluid communication with a breathing tube;
   b) a line port in fluid communication with a ventilator line;
   c) a means for inserting and retracting a catheter into and out of the breathing tube;
   d) a means for irradiating at least a portion of the catheter with ultraviolet radiation to sterilize the catheter while the breathing tube is connected to a patient; and
   e) a means for absorbing the ultraviolet radiation to prevent a substantial portion of radiation from leaving the respiratory circuit junction and striking the patient.

18. A respiratory circuit junction as recited in claim 17, further comprising a means for irradiating at least a portion of the inner surface of the respiratory circuit junction to sterilize the inner surface.

19. A respiratory circuit junction as recited in claim 17, further comprising an additional line port.

20. A respiratory circuit junction as recited in claim 19, further comprising one or more light sources located adjacent to the additional port.

* * * * *